US012773478B2

(12) United States Patent
Sherman et al.

(10) Patent No.: US 12,773,478 B2
(45) **Date of Patent: *Oct. 27, 2026**

(54) COATED TUBING FOR MEDICAL ARTICLES

(71) Applicant: Solventum Intellectual Properties Company, Maplewood, MN (US)

(72) Inventors: Audrey A. Sherman, Woodbury, MN (US); Daniel J. Rogers, Grant, MN (US); Matthew T. Scholz, Woodbury, MN (US)

(73) Assignee: Solventum Intellectual Properties Company, Eagan, MN (US)

( * ) Notice: Subject to any disclaimer, the term of this patent is extended or adjusted under 35 U.S.C. 154(b) by 911 days.

This patent is subject to a terminal disclaimer.

(21) Appl. No.: 17/926,449

(22) PCT Filed: Apr. 6, 2021

(86) PCT No.: PCT/IB2021/052861

§ 371 (c)(1),
(2) Date: Nov. 18, 2022

(87) PCT Pub. No.: WO2021/240254

PCT Pub. Date: Dec. 2, 2021

(65) Prior Publication Data

US 2023/0181800 A1 Jun. 15, 2023

Related U.S. Application Data

(60) Provisional application No. 63/030,350, filed on May 27, 2020.

(51) Int. Cl.

| | |
|---|---|
| ***A61L 29/04*** | (2006.01) |
| ***A61L 29/08*** | (2006.01) |
| ***A61L 31/08*** | (2006.01) |

(52) U.S. Cl.

CPC ............... *A61L 29/04* (2013.01); *A61L 29/08* (2013.01); *A61L 31/08* (2013.01)

(58) Field of Classification Search

None

See application file for complete search history.

(56) References Cited

U.S. PATENT DOCUMENTS

| | | | |
|---|---|---|---|
| 7,030,244 | B2 | 4/2006 | Cyr et al. |
| 7,060,829 | B2 | 6/2006 | Cyr et al. |

(Continued)

FOREIGN PATENT DOCUMENTS

| | | | |
|---|---|---|---|
| CN | 103132045 | A | 6/2013 |
| DE | 2622502 | A1 | 11/1977 |

(Continued)

OTHER PUBLICATIONS

International Search Report received for PCT International Application No. PCT/IB2021/052861, mailed on Jul. 6, 2021, 4 pages.

(Continued)

*Primary Examiner* — Thomas J Kessler

(57) ABSTRACT

Polymeric tubing containing extractable component(s) for use in medical articles include a tube and a vapor-deposited coating of a barrier polymer covering at least a portion of the tube. The barrier polymer is derived from at least one ethylenically unsaturated monomer. The vapor-deposited polymer coating reduces the extraction of extractable component(s) from the tube. The barrier polymer is parylene or a copolymer of parylene. The polymer coated tubing can be used in stethoscopes.

19 Claims, 4 Drawing Sheets

(56) References Cited

U.S. PATENT DOCUMENTS

| | | | | |
|---|---|---|---|---|
| 7,105,688 | B2 | 9/2006 | Pearson et al. | |
| 7,138,539 | B2 | 11/2006 | Cyr et al. | |
| 7,141,685 | B2 | 11/2006 | Cyr et al. | |
| 7,172,634 | B2 | 2/2007 | Pearson et al. | |
| 7,179,308 | B2 | 2/2007 | Pearson et al. | |
| 7,659,325 | B2 | 2/2010 | Hagting et al. | |
| 7,662,937 | B2 | 2/2010 | Satake et al. | |
| 8,865,929 | B2 | 10/2014 | Xu et al. | |
| 2008/0093157 | A1* | 4/2008 | Drummond .............. | A61B 7/02 181/131 |
| 2010/0266794 | A1* | 10/2010 | Wright ................ | C08F 290/061 264/496 |
| 2013/0045146 | A1* | 2/2013 | Peters ................... | B01L 3/5635 422/547 |
| 2015/0165097 | A1* | 6/2015 | Parthasarathy ......... | A61L 31/16 514/340 |

FOREIGN PATENT DOCUMENTS

| | | | |
|---|---|---|---|
| EP | 1830712 | A1 | 9/2007 |
| WO | 2006022854 | A1 | 3/2006 |
| WO | 2008022258 | A3 | 2/2008 |
| WO | 2008039749 | A3 | 4/2008 |

OTHER PUBLICATIONS

Rahman, "The Plasticizer Market: An Assessment of Traditional Plasticizers and Research Trends to Meet New Challenges", Progress in Polymer Science, 2004, vol. 29, No. 12, pp. 1223-1248.

* cited by examiner

COATED TUBING FOR MEDICAL ARTICLES

FIELD OF THE DISCLOSURE

The current disclosure relates to methods for coating of polymeric tubing for use in medical articles.

BACKGROUND

Medical devices and articles utilize a wide range of polymeric materials. Among the materials used are polyvinyl chloride (PVC) often referred to as "vinyl". PVC by itself is a rigid material, and thus plasticizers are added to the material to make it softer and more flexible. Among the commonly used plasticizers are phthalates. In recent years, the use of phthalate plasticizers in PVC for medical uses has fallen into disfavor, and phthalate-free PVC materials are being used more and more in medical applications. However, as is well known in the chemical arts, making a change in composition often causes changes in the properties of the materials.

SUMMARY

The current disclosure relates to medical articles with polymer coated tubing and methods of preparing such articles. In some embodiments, the medical articles comprise a tube with an interior surface and an exterior surface, where the tube comprises a polymer composition containing one or more extractable components, and a vapor-deposited coating of a barrier polymer covering at least a portion of at least the exterior surface of the tube. The vapor-deposited barrier polymer is derived from at least one ethylenically unsaturated monomer. The vapor-deposited polymer coating barrier reduces the extraction of extractable component(s) from the tube. In some embodiments, the vapor-deposited barrier polymer is parylene or copolymers of parylene. Among the medical articles that utilize the barrier polymer coated tubing are stethoscopes.

Also disclosed are methods of preparing medical articles. In some embodiments, the method of preparing a medical article comprises providing a polymeric tube with an interior surface and an exterior surface, and vapor coating a barrier polymer onto at least a portion of at least the exterior surface of the tube. The polymeric tube comprises a polymer composition containing one or more extractable components. The barrier polymeric tube comprises at least one ethylenically unsaturated monomer. In some embodiments, the vapor-deposited barrier polymer is parylene or copolymers of parylene.

BRIEF DESCRIPTION OF THE DRAWINGS

The present application may be more completely understood in consideration of the following detailed description of various embodiments of the disclosure in connection with the accompanying drawings.

Figure 1:
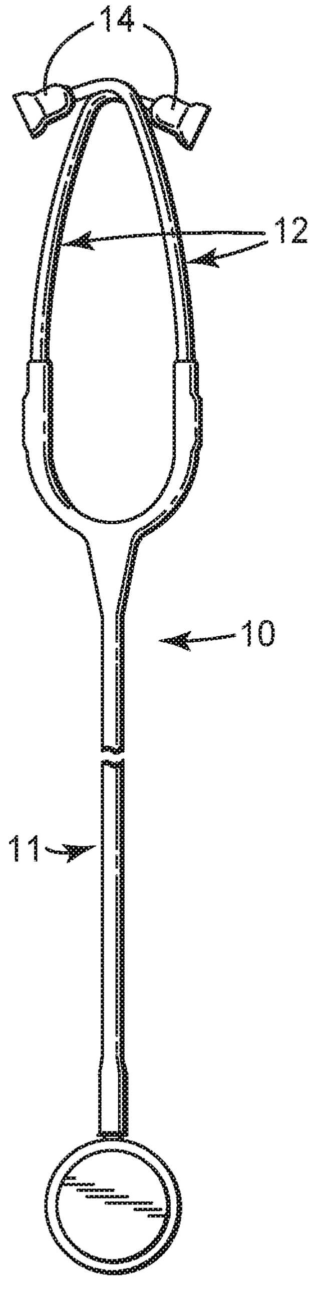
FIG. 1 is a top view of a stethoscope incorporating a tubing article of this disclosure.

In the following description of the illustrated embodiments, reference is made to the accompanying drawings, in which is shown by way of illustration, various embodiments in which the disclosure may be practiced. It is to be understood that the embodiments may be utilized and structural changes may be made without departing from the scope of the present disclosure. The figures are not necessarily to scale. Like numbers used in the figures refer to like components. However, it will be understood that the use of a number to refer to a component in a given figure is not intended to limit the component in another figure labeled with the same number.

DETAILED DESCRIPTION

Medical devices and articles utilize a wide range of polymeric materials. Among the materials used are polymers that contain extractable materials such as plasticizers, fillers, tackifiers, heat stabilizers, and the like. These extractable materials are often present in large quantities. The extractable materials can be extracted from the polymer by exposure to solvents, by heat, by contact with fluids such as aqueous or hydroalcoholic disinfectants, by high humidity (e.g. >90% relative humidity), by contact with skin, or even over time. This extraction is undesirable for many reasons and can cause difficulties in the use of the medical articles.

One particularly useful polymeric material is polyvinyl chloride (PVC) often referred to as "vinyl". PVC by itself is a rigid material, and thus plasticizers are added to the material to make it softer and more flexible. Among the commonly used plasticizers are phthalates. In recent years, the use of phthalate plasticizers in PVC for medical uses has fallen into disfavor, and phthalate-free PVC materials are being used more and more in medical applications. However, as is well known in the chemical arts, making a change in composition often causes changes in the properties of the materials.

PVC materials are frequently used in tubing materials, such as the sound transmitting tubes of stethoscopes. These tubes have a variety of required property features. Among these properties are flexibility, resistance to degradation from exposure to heat and chemicals, durability, an aesthetically pleasant look, and a pleasant feel. The introduction of phthalate-free PVC materials has been observed to adversely affect some or all of these properties. As the stethoscopes are used, washing, and exposure to the body heat of the user tends to cause the PVC material to become more rigid as plasticizer leaches out or is washed away.

In this disclosure, it has been found that coating of polymeric tubes that contain extractable components with a vapor-deposited coating of a polymer derived from at least one ethylenically unsaturated monomer not only reduces the extractability of the extractable components, but also provides a variety of additional desirable features. Among these features are optical and tactile features such as the color, the texture, the coefficient of friction, the optical appearance of the tubing, or a combination thereof. Because the coating protects the tubing, the tubing retains its desirable properties over the lifetime of the article.

Disclosed herein are tubes useful in tubing articles, where the tubes comprise a polymer composition containing one or more extractable components that have a vapor-deposited coating of a barrier polymer derived from at least one ethylenically unsaturated monomer on at least the exterior surface of the tube. In some embodiments, the vapor-deposited coating is present on both the interior and exterior surface of the tube. The barrier polymer is derived from at least one ethylenically unsaturated monomer and may be optionally crosslinked by incorporation of at least one dimeric ethylenically unsaturated monomer. The vapor-deposited barrier polymer coating reduces the extraction of extractable component(s) from the tube. Also disclosed are methods of preparing tubing articles, such as medical articles. Among the tubing articles are stethoscopes.

Unless otherwise indicated, all numbers expressing feature sizes, amounts, and physical properties used in the specification and claims are to be understood as being modified in all instances by the term "about." Accordingly, unless indicated to the contrary, the numerical parameters set forth in the foregoing specification and attached claims are approximations that can vary depending upon the desired properties sought to be obtained by those skilled in the art utilizing the teachings disclosed herein. The recitation of numerical ranges by endpoints includes all numbers subsumed within that range (e.g. 1 to 5 includes 1, 1.5, 2, 2.75, 3, 3.80, 4, and 5) and any range within that range.

As used in this specification and the appended claims, the singular forms "a", "an", and "the" encompass embodiments having plural referents, unless the content clearly dictates otherwise. For example, reference to "a layer" encompasses embodiments having one, two or more layers. As used in this specification and the appended claims, the term "or" is generally employed in its sense including "and/or" unless the content clearly dictates otherwise.

The term "tube" and "tubing" as used herein refers to a three-dimensional tubular article that is cylindrically symmetric. Tubes and tubing are defined by an inner diameter, an outer diameter, (the thickness of the tubing is the difference between the outer diameter and the inner diameter) and a length. While the thickness of the tubing can vary slightly through the length of the tube as the result of the method of preparation, etc., no intentional asymmetries are present in the tubing. Typically the length is substantially greater than the diameter of the tube.

The term "(meth)acrylate" refers to monomeric acrylic or methacrylic esters of alcohols. Acrylate and methacrylate monomers or oligomers are referred to collectively herein as "(meth)acrylates". Materials referred to as "(meth)acrylate functional" are materials that contain one or more (meth) acrylate groups.

The terms "polysiloxane" and "siloxane-based" as used herein refer to polymers or units of polymers that contain siloxane units. The terms silicone or siloxane are used interchangeably and refer to units with dialkyl or diaryl siloxane ($-SiR_2O-$) repeating units.

The terms "room temperature" and "ambient temperature" are used interchangeably to mean temperatures in the range of 20° C. to 25° C.

The terms "polymer" and "macromolecule" are used herein consistent with their common usage in chemistry. Polymers and macromolecules are composed of many repeated subunits. As used herein, the term "macromolecule" is used to describe a group attached to a monomer that has multiple repeating units. The term "polymer" is used to describe the resultant material formed from a polymerization reaction.

The term "alkyl" refers to a monovalent group that is a radical of an alkane, which is a saturated hydrocarbon. The alkyl can be linear, branched, cyclic, or combinations thereof and typically has 1 to 20 carbon atoms. In some embodiments, the alkyl group contains 1 to 18, 1 to 12, 1 to 10, 1 to 8, 1 to 6, or 1 to 4 carbon atoms. Examples of alkyl groups include, but are not limited to, methyl, ethyl, n-propyl, isopropyl, n-butyl, isobutyl, tert-butyl, n-pentyl, n-hexyl, cyclohexyl, n-heptyl, n-octyl, and ethylhexyl.

The term "aryl" refers to a monovalent group that is aromatic and carbocyclic. The aryl can have one to five rings that are connected to or fused to the aromatic ring. The other ring structures can be aromatic, non-aromatic, or combinations thereof. Examples of aryl groups include, but are not limited to, phenyl, biphenyl, terphenyl, anthryl, naphthyl, acenaphthyl, anthraquinonyl, phenanthryl, anthracenyl, pyrenyl, perylenyl, and fluorenyl.

The terms "free radically polymerizable" and "ethylenically unsaturated" are used interchangeably and refer to a reactive group which contains a carbon-carbon double bond which is able to be polymerized via a free radical polymerization mechanism.

As used herein the term "PVC" is used as a shorthand definition of polyvinyl chloride. The term "phthalate-free PVC" as used herein refers to a PVC material that does not contain phthalate plasticizer.

As used herein the term "plasticizer" refers to a compound(s) which when added to a polymer results in increased flexibility.

As used herein the term "parylene" is a trade name for a variety of chemical vapor deposited poly(p-xylylene) polymers. The term is used herein as a generic name for members of a unique polymer series. The basic member of the series, called Parylene N, is poly-para-xylylene, a completely linear, highly crystalline material.

Parylene C, the second commercially available member of the series, is produced from the same monomer modified by the substitution of a chlorine atom for one of the aromatic hydrogens. The structures are shown in FIG. 1. Parylene N, C & D Chemical Structures.

Parylene D, the third member of the series, is produced from the same monomer modified by the substitution of the chlorine atom for two of the aromatic hydrogens. Parylene D is similar in properties to Parylene C with the added ability to withstand higher use temperatures.

The parylene also may have one or more hydrogen atoms replaced by fluorine. For example, Parylene AF-4 and parylene VT-4 (generic name, per-fluorinated aromatic ring).

Parylene X is a crosslinkable parylene. Poly(methyl-p-xylylene) or parylene M

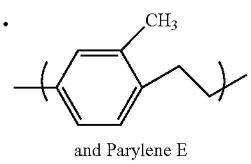

and Parylene E

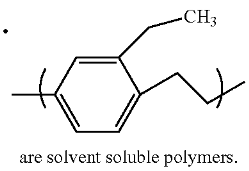

are solvent soluble polymers.

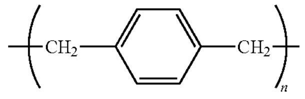

Parylene N

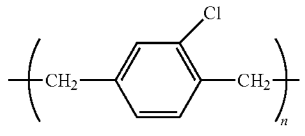

Parylene C

-continued

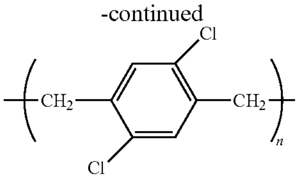

Parylene D

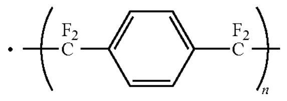

PARYLENE AF-4

As used herein "parylene copolymers" are chemical vapor deposited derived from p-xylylene and at least one additional ethylenically unsaturated monomer.

Disclosed herein are tubes useful to prepare tubing articles, especially medical articles. The tubes have an interior surface and an exterior surface and are prepared from a polymer composition containing one or more extractable components. The tubes further have a vapor-deposited coating of a barrier polymer derived from at least one ethylenically unsaturated monomer covering at least the exterior surface of the tube. The vapor-deposited barrier polymer coating reduces the extraction of extractable component(s) from the tube.

A wide range of polymer compositions containing one or more extractable components are suitable for preparing tubes. In some embodiments, the polymer compositions comprise plasticized polyvinyl chloride (PVC), plasticized PVC copolymers, plasticized polyurethane, or polysiloxanes. Polysiloxanes may or may not include plasticizers like the other classes of polymers, but even if plasticizers are not used in the polysiloxanes, they may contain a variety of extractable materials such as unreacted cyclic siloxane, catalyst residue, tackifier, or a combination thereof. Additionally, any of the above polymer compositions may contain additional materials that may be extractable including stabilizing agents such as thermal stabilizers and UV stabilizers, fillers, and the like.

Polyurethane polymers are well known in the polymer arts, being prepared from the reaction of poly-isocyanates and polyols. A wide range of polyurethane polymers are suitable, including aromatic, aliphatic, urethane block copolymers and copolymers and mixtures thereof. A wide range of plasticizers can be used to plasticize the polyurethane polymers. The polyurethanes may be linear or crosslinked. The polyols used to prepare the polyurethanes may be poly-ether polyols, polyester polyols, aliphatic polyols, siloxane polyols, and the like. The crosslinked polyurethanes are generally made via a 2 part reaction.

Polysiloxane polymers are also well known in the art. Typically, siloxane-based polymers can be prepared in a variety of ways including moisture-curing, hydrosilylation, and condensation reactions. Additionally, a wide range of polysiloxane polymers and polysiloxane precursors are commercially available. As mentioned above, the polysiloxanes can contain a variety of extractable components. Additionally, it can be desirable to apply a barrier coating to polysiloxane tubes, not only as a barrier against leaching of extractable components but also to alter the surface properties of the polysiloxane tube. Polysiloxanes often have a tacky or sticky feel that can be undesirable. Additionally, while efforts are typically expended to ensure that no residual siloxane monomer is present in the polymer that is formed into a tube, these tasks can be labor intensive or expensive and can be avoided through the use of a barrier layer that inhibits or prevents the leaching of extractable material from the polymeric tube.

In many embodiments, the polymer compositions comprise plasticized PVC polymers and plasticized PVC copolymers. PVC copolymers are prepared by copolymerizing one or more ethylenically unsaturated co-monomers with vinyl chloride. An example of a PVC copolymer is polyvinyl chloride-vinyl acetate. Like the PVC polymers described below, the PVC copolymers typically contain plasticizers, often relatively high loadings of plasticizer.

One particularly suitable class of polymers for tubing articles, especially medical tubing articles are PVC polymers. PVC polymers tend to be rigid materials, and therefore plasticizers are added to make the polymers flexible. Typically, the PVC polymer compositions contain a large quantity of plasticizer. The PVC polymer compositions typically contain up to 50-60% by weight plasticizer based on the total weight of the tube composition. In some embodiments, the PVC polymer composition comprises at least 20% by weight plasticizer, typically at least 30% by weight plasticizer, more typically at least 35% by weight plasticizer, or even at least 40% or 45% by weight plasticizer by weight. Generally, the PVC polymer compositions comprise less than 60% by weight plasticizer or less than 55% by weight plasticizer.

As was mentioned above, the use of phthalate-free plasticizers is becoming more prevalent in the preparation of medical articles such as tubing articles. In some embodiments, the polymer composition of the tubes of this disclosure comprise PVC polymer compositions that are free of phthalate plasticizers.

Among the suitable classes of plasticizers are oligomeric or polymeric plasticizers having an average molecular weight of greater than 1000 Daltons, greater than 1500 Daltons, or even greater than 2000 Daltons as determined by GPC with the appropriate standards. Particularly suitable oligomeric or polymeric plasticizers are aliphatic or aromatic polyesters and are available from Hallstar under the PLASTHALL tradename or from Lanxess under the ULTRAMOL brandname.

Another suitable class of plasticizers are sulfonate esters such as MESAMOLL which is an alkylsulphonic acid ester with phenol.

Additional plasticizers include trimellitates such as trimethyl trimellitate, tri-(2-ethylhexyl) trimellitate, tri-(heptyl, nonyl) trimellitate and the like.

Aliphatic dicarboxylic acid-based plasticizers such as bis(2-ethylhexyl)adipate dimethyl adipate, dioctyl adipate, dibutyl sebacate, dibutyl maleate and the like.

Other plasticizers include azelates, benzoates, terephthalates such as dioctyl terephthalate/DEHT (Eastman Chemical Company Trademark: EASTMAN 168), 1,2-Cyclohexane dicarboxylic acid diisononyl ester (BASF trademark: HEXAMOLL DINCH).

Sulfonamides such as N-ethyl toluene sulfonamide (o/p ETSA), ortho and para isomers, glycols and polyethers such as triethylene glycol dihexanoate and tetraethylene glycol diheptanoate.

The polymeric tubes of this disclosure may have a wide range of diameters and thicknesses. Typically, the tubes are not wide tubes, often having an inner diameter of from 1 to 10 millimeters. In some embodiments, the tube has a thickness of from 0.1-7 millimeters. Generally, the tubes are at least 20 centimeters in length, more typically at least 40 centimeters in length.

The tubes of this disclosure also have a vapor-deposited coating of a barrier polymer derived from at least one ethylenically unsaturated monomer covering at least a portion of the exterior surface of the tube. For example, stethoscope tubing is desirably coated at least along the part of the tubing which would contact the skin when worn around the neck. In many embodiments, the entire exterior surface of the tube has a vapor-deposited coating of a barrier polymer. In some embodiments, the tube also has a vapor-deposited coating of a barrier polymer on the interior surface of the tube.

The vapor-deposited coating of a barrier polymer comprises parylene or a copolymer of parylene. Parylene is the trade name for vapor-deposited poly-para-xylylene. Poly para-xylylene, also referred to as parylene N, is shown in Formula 1 below:

Formula 1

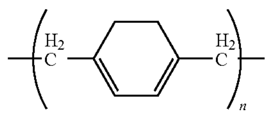

Parylene is prepared when the precursor [2,2]paracyclophane (shown in Formula 2 below) is heated above 550° C. in vacuum. Upon condensation on a surface, the poly-para-xylylene forms.

Formula 2

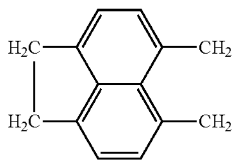

In some embodiments, the vapor-deposited coating of a crosslinked vinyl polymer comprises parylene, that is to say parylene N. In other embodiments, the vapor-deposited coating of a crosslinked vinyl polymer comprises a substrituted parylene such as parylene C. Parylene C has the general structure shown in Formula 3 below. Parylene C is prepared by using a chlorine-substituted dimer.

Formula 3

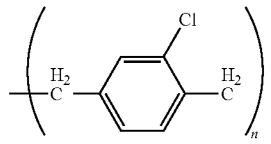

In some embodiments, the vapor-deposited coating of a barrier polymer comprises a copolymer of parylene and at least one (meth)acrylate. A wide variety of (meth)acrylates are suitable. In some embodiments, the (meth)acrylate comprises at least one $C_3$-$C_{18}$ alkyl (meth)acrylate.

The vapor-deposited coating of a barrier polymer can have a wide range of thicknesses. As mentioned above, the coating may be a continuous coating, present on the entire exterior surface of the tubing or it can be present in selective regions of the exterior surface of the tubing. Additionally, the coating may be present on both the interior and exterior surfaces of the tubing. In some embodiments, the vapor-deposited barrier polymer coating has a thickness of from 1-10 micrometers. In other embodiments, the vapor-deposited crosslinked vinyl polymer coating has a thickness of from 2-5 micrometers. The coating may have a uniform or essentially uniform thickness, or the coating thickness may vary over the surface of the tubing. Typically, the coating has an essentially uniform thickness.

The vapor-deposited coating of a barrier polymer may comprise additional additives. Among the additives are heat stabilizers, coloring agents, mold release agents, and antimicrobial agents.

One necessary feature of the barrier polymers is their ability to strongly adhere to the tube. This is complicated by the fact that typically the tubing polymeric compositions contain high levels of plasticizer. Among the circumstances that make strong adhesion necessary is in bending. It is desirable that the barrier polymers are able to withstand 180° bending of the tubing for at least 5,000 cycles, more desirably at least 10,000 cycles and even more desirably at least 20,000 cycles when tested according to the "Bend Test" disclosed in the Examples Section below.

The vapor-deposited coatings of a barrier polymer of the current disclosure reduce the extractability of the extractable components of the polymer compositions of the tubing. In some embodiments, the coatings prevent the extraction of extractable components from the polymer compositions of the tubing. This extraction refers to a variety of extraction methods. It is particularly desirable that the barrier polymers prevent extraction by both polar fluids such as aqueous and hydroalcoholic (e.g. rubbing alcohol, 70/30 v/v isopropanol water) disinfectants as well as nonpolar fluids such as skin oil (sebum) and synthetic sebum. Examples of extraction methods include solvent extraction, heat extraction, and skin contact extraction. Solvent extraction involves the application of solvent to the polymer composition surface. Suitable solvents are described above and include polar fluids and nonpolar fluids. Upon removal of the solvent by wiping or similar techniques results in extractable components leaving the polymer composition. Heat extraction involves applying heat to the polymer composition which results in the extractable components leaching from the polymer composition. Heat can be used alone or in combination with the solvent extraction method described above. Skin contact extraction results from the contact of skin to the polymer composition where the extractable components in the polymer composition leach from the polymer composition. In practice, medical devices containing tubing articles can encounter each of these extraction methods, or a combination of them. The tubing article may be washed or cleaned with a solvent or other liquid, or the tubing may come into contact with a variety of fluids. Heat extraction can occur from contact with, for example, body heat, or higher temperatures such as, for example 50° C. if the article is left in a vehicle on a hot day. Similarly, skin contact extraction can occur from exposure of the tubing article to skin.

The extractability of extractable components from a polymer composition can be modeled in a variety of ways. Among the useful methods are those described in the Examples section.

Besides the reduction of extractability of the extractable components of the polymer composition of the tubing, the coatings of the current disclosure can affect other properties of the tubing. In some embodiments, the vapor-deposited coating changes the color, the texture, the coefficient of friction, the optical appearance of the tubing, or a combination thereof. This can be particularly true of polysiloxane tubes which, as described above, can have a tacky or sticky feel. Additionally, if the coating is present only in certain regions, the coating can contain coloring agents to provide a patterned appearance as well as the functional advantages discussed above. For example, the tubing could be partially masked such that only selective regions of the surface of the tubing is coated. Suitable coloring agents include fluorescent or visible light reactive ethylenically unsaturated dyes. Examples of suitable dyes include the fluorescent ethylenically unsaturated dyes: fluorescein dimethacrylate; Nile Blue (meth)acrylamide; (meth)acryloxyethyl thiocarbamoyl Rhodamine B; 9-anthracenylmethyl methacrylate; 2-naphthyl methacrylate. Examples of visible light reactive dyes include ethylenically unsaturated red or blue anthraquinone dyes and other ethylenically unsaturated colorants materials as described in U.S. Pat. Nos. 8,865,929; 7,662,937; 7,659,325; 7,179,308; 7,172,634; 7,141,685; 7,138,539; 7,105,688; 7,060,829; 7,030,244.

The coated tubing of the current disclosure can be used to prepare a wide variety of medical articles. One particularly suitable use is for the tubing of stethoscopes. A typical stethoscope is shown in FIG. 1. FIG. 1 shows a top view of stethoscope 10. Stethoscope 10 has tubing 11 attached to dual sound transmitting tubes 12, terminating in ear tips 14. The elements of stethoscope 10 can vary from those shown, but the fundamental elements are present. This disclosure relates to tubing 11. The reduction of extractability of plasticizer desirable features of the tubing 11. Among these features are flexibility, handleability, and pleasing aesthetics. In many cases tubing 11 is prepared from plasticizer-filled PVC polymer. Flexibility is imparted to the PVC polymer by high levels of plasticizer, and retention of this plasticizer within the polymer matrix, in other words the lack of plasticizer extraction, is important to the usefulness of the tubing. Because the PVC polymer, or other polymeric material if used, often have high levels of plasticizer or other extractable components, migration of the plasticizer out of the polymer can occur over time, or the plasticizer can be extracted by washing or cleaning, or by contact with skin either when worn or when handled. Loss of flexibility of the tubing reduces the usefulness of the stethoscope. Handleability relates to the feel of the tubing, which is going to be worn and handled by the user of the stethoscope. Another important feature of handleability also relates to the lack of plasticizer extraction in that if plasticizer exudes from the tubing, the feel of the tubing becomes unpleasant and plasticizer can be transferred to the user's hand. A variety of aesthetic features are desirable including the color, texture, gloss, and feel are desirable for the tubing of the stethoscope. Because the tubing comes into frequent contact with skin, the texture and feel of the tubing should be aesthetically pleasant, meaning that the tubing should be smooth and have a low coefficient of friction.

As mentioned above, the coated tubing of the present disclosure provides these desirable features. The coatings not only inhibit the extraction of plasticizer or other extractable components from the polymeric tubing, but also the coatings can provide desirable handleability and aesthetic features.

Also disclosed are methods for preparing medical articles. In some embodiments, the method comprises providing a tube with an interior surface and an exterior surface, and vapor coating a barrier polymer derived from at least one ethylenically unsaturated monomer onto at least a portion of the exterior surface of the tube. The barrier polymer may be coated on the entire exterior surface of the tube and may also be coated on the interior surface of the tube, as has been described above. The polymeric tubing has been described above and comprises a polymer composition containing one or more extractable components.

In some embodiments, vapor coating a barrier polymer onto at least a portion of the exterior surface of the tube comprises placing the tube in a deposition chamber, applying a vacuum to the deposition chamber, heating a precursor material to volatize and optionally pyrrolyze at least a portion of it, and introducing the volatilized and optionally pyrrolyzed percursor material into the deposition chamber. The precursor material comprises the at least one ethylenically unsaturated monomer. Typically, the precursor material comprises parylene or a mixture of parylene and at least one (meth)acrylate. Suitable parylene compositions are described above. As was described above, the volatilized precursor material deposits on the tubing and polymerizes to form the barrier coating on the tubing surface. At least a portion of the exterior surface of the tubing is coated, and in many embodiments, the entire exterior surface of the tubing is coated. In some embodiments, both the interior and exterior surface of the tubing is coated.

There are a variety of methods for placing the tubing in the deposition chamber. In some embodiments, the tubing may be placed on a rotating basket or it may be hung from a rack in the deposition chamber.

The tubing suitable for use in the methods of this disclosure are polymeric compositions with extractable components. Examples of suitable polymeric compositions have been described above. In some embodiments, the polymer compositions comprise plasticized polyvinyl chloride (PVC), plasticized PVC copolymers, plasticized polyurethane, or polysiloxanes. Polysiloxanes may or may not include plasticizers like the other classes of polymers, but even if plasticizers are not used in the polysiloxanes, they may contain a variety of extractable materials such as unreacted cyclic siloxane, catalyst residue, tackifier, plasticizer, or a combination thereof. Additionally, any of the above polymer compositions may contain additional materials that may be extractable including stabilizing agents such as thermal stabilizers and UV stabilizers, fillers, and the like.

The polymeric tubes of this disclosure may have a wide range of diameters and thicknesses. Typically, the tubes are not wide tubes, often having an internal diameter of from 1 to 10 millimeters. In some embodiments, the tube has a thickness of from 0.1-7 millimeters. The tube may have a variety of lengths, typically at least 20 centimeters, often at least 40 centimeters.

The vapor-deposited crosslinked polymer coatings have been described above. Typically, the polymer coating has a thickness of from 1-10 micrometers. In some embodiments, the polymer coating has a thickness of from 2-5 micrometers.

As mentioned above, the coated tubing can be used to prepare a wide variety of medical articles. In some embodiments, the coated tubes are used in stethoscopes, as has been described above.

Figure 2:
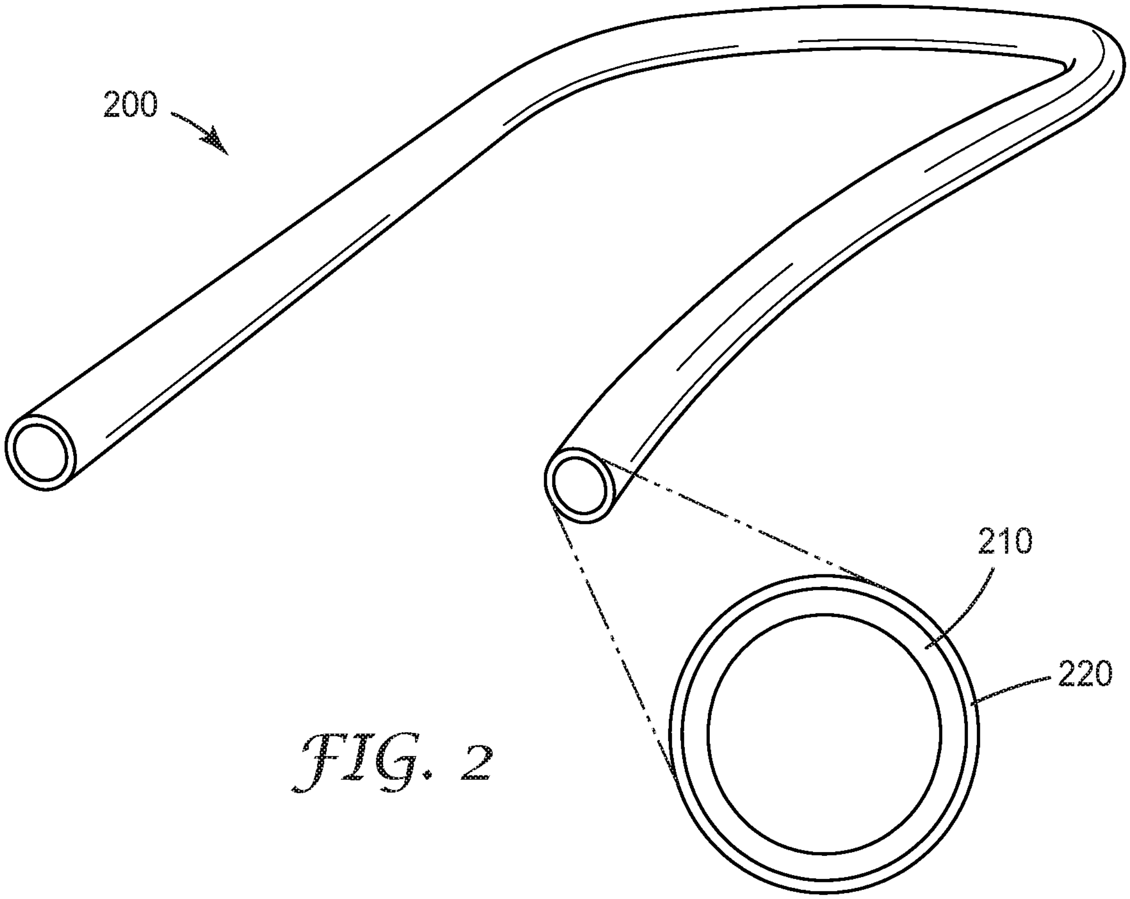
FIG. 2 is a top view of coated tubing of this disclosure, including a cross sectional view of a segment of the coated tubing.

An embodiment of coated tubing is shown in FIG. 2. In FIG. 2, tubing article 200 comprises tubing layer 210 and coating layer 220. Coating layer 220 is a vapor-deposited barrier polymer coating as described above. Also included in FIG. 2 is a close up of a cross-section of tubing article 200.

Figure 3:
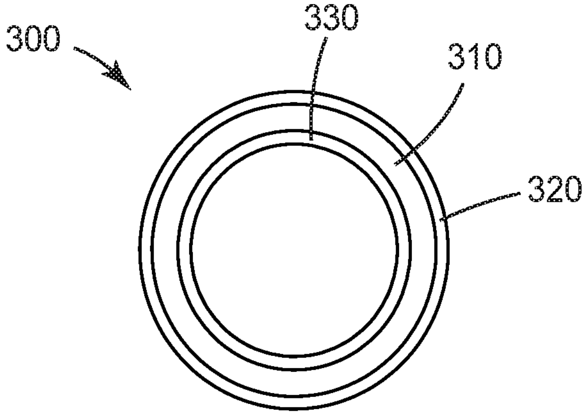
FIG. 3 is a cross sectional view of a segment of another embodiment of coated tubing of this disclosure.

FIG. 3 shows a cross-sectional view of a segment of coated tube 300. Coated tube 300 includes tubing layer 310, outer coating layer 320, and inner coating layer 330. Outer coating layer 320 and inner coating layer 330 are vapor-deposited barrier polymer coatings as described above.

Examples

These examples are merely for illustrative purposes only and are not meant to be limiting on the scope of the appended claims. All parts, percentages, ratios, etc. in the examples and the rest of the specification are by weight, unless noted otherwise.

Sample Preparation

Parylene Coating Process

The stethoscope tubes used in these Examples were polyvinyl chloride (PVC) sound transmission tubes prepared with a phthalate-free poly(vinyl chloride) (PVC) formulation, and are used in the manufacture of LITTMANN Cardiology stethoscopes (3M Company, St. Paul, MN). The PVC plastisol formulations were made with different color pigments that provided dip coated PVC sound transmission tubes with similar properties. Both color tubes were flexible and elastomeric having a composition very similar to that shown in Table 3 below. The exteriors of the uncoated sound transmission tubes were wiped once with a lab wipe wetted with isopropanol (IPA) and allowed to dry prior to loading into the reactor. The tubes were coated using a vacuum process at approximately 160 milliTorr while either statically hung from a rotating carousel or while tumbled in a cylindrical wire cage. Sample lots of the tubes were coated with 2.3 micrometer thick coatings of either Parylene-C or Parylene-N. The coating process coated both interior and exterior surfaces of the tubing.

Prior to coating, the PVC sound transmission tubes had a glossy finish and slightly tacky feel with a relatively high coefficient of friction. After application of either of the Parylene-C or Parylene-N coating, the Parylene-coated sound transmission tubes had a dry, slippery feel and a lower coefficient of friction. Sound transmission tubes coated with Parylene-N had a uniform matte finish. Sound transmission tubes coated with Parylene-C remained glossy in appearance but had a fine elephant-skin finish. Sound transmission tubes coated using the wire cage method showed occasional scuff marks, but all the coatings were fully functional and conformal. Tubing flexibility was not noticeably changed with either coating. (Sample testing of flat sheets of coated and uncoated PVC is presented below for CoF (coefficient of friction) against hair and simulated skin.)

Sample Testing

Adhesion and Bend Testing

The coated tubing samples were tested for adhesion of the coating to the tubing and for bending to ensure that the coating remained adhered to the tubing upon bending. Because of the shape and limited surface area of tubing samples, modified testing techniques were used.

Adhesion testing: A modified test method similar to ASTM 3359 was used to determine the adhesion of the coating to the tubing. A cross hatch pattern was cut into the coating with a scalpel and a pressure sensitive adhesive tape was attached to the cross hatched surface and removed. Additionally, a tweezer was used to attempt to lift off the edges of the cross hatch pattern of the coating. All coated samples passed this adhesion testing.

Bend testing: Approximately 6 inches of barrier polymer coated tubing was fixed to a hinged flat panel with adhesive tape leaving approximately 1 inch (2.54 centimeters) of free tubing at the hinge point. The device bent the tubing approximately 150 degrees and back again completing approximately 20 cycles/minute. The samples were cycled for 300,000 cycles with no visible deterioration of the coating.

Solvent Extraction Testing

The ability of the Parylene-C and Parylene-N coatings to reduce the extraction of material from the sound transmission tubes was evaluated using a solvent extraction method. Samples of tubing were prepared by cutting the tubing into 1 inch (2.54 centimeters) pieces and sealing the ends using a hot plate set at 220° C. covered with aluminum foil. These tubing samples were then coated with Parylene-C or Parylene-N. Each tubing sample was placed in a 40 mL vial and filled with 37 mL of a 60:40 solvent mixture of isopropanol and acetone (volume/volume). The vials were then aged at ambient laboratory temperature for the time provided in Table 1. The samples were removed from the vials and residual solvent mixture was removed by drying in a 50° C. oven until a constant weight was achieved. Absorption of the solvent mixture by the PVC may result in a net weight gain, in which case the weight loss is reported as a negative number. The results are reported in Table 1 and the reported percent mass loss is an average of multiple tests.

TABLE 1

Percentage weight loss of material from ear tubes extracted with 60:40 isopropanol and acetone.

| PVC tubing type | Coating type | Extraction time | Mass loss |
|---|---|---|---|
| Sample B | None (comparative) | 2 hours | 8.7% |
| | | 4 hours | 12.4% |
| Sample P | None (comparative) | 2 hours | 5.5% |
| | | 4 hours | 7.6% |
| Sample P | Parylene-N | 2 hours | 1.2% |
| | | 4 hours | 2.1% |
| Sample P | Parylene-C | 2 hours | 0.0% |
| | | 4 hours | −0.1% |

The vacuum deposited Parylene treatments resulted in a dramatic reduction in the loss of plasticizer without compromising the flexibility and strength of the stethoscope tubing,

Skin Oil Extraction Testing

The ability of the Parylene-C and Parylene-N coatings to reduce the extraction of material from the sound transmission tubes was also evaluated using a skin oil extraction model. This test used a synthetic skin oil formulation to model extended contact of the sound transmission tubes with human skin. The synthetic skin oil was made by mixing 70% olive oil, 20% oleic acid, and 10% squalene until uniform. The tubing samples were prepared using the plastisol formulation shown in Table 3, using the sample preparation method presented below. Samples 1, 2, and 3 were uncoated, Samples B and N were coated. Samples of tubing were prepared by cutting the tubing into 1 inch (2.54 centimeters) pieces and sealing the ends using a hot plate set at 220° C. and covered with aluminum foil. These tubing samples were then coated with Parylene-C or Parylene-N. Each tubing sample was placed in a 40 mL vial and filled with 37 mL of the synthetic skin oil. The vials were then placed in a 50° C. oven for a period of time as provided in Table 2. The vials were removed from the oven and the samples rinsed with IPA and wiped with a paper towel to remove synthetic skin oil from the surface. Residual IPA was removed by drying in a 50° C. oven until a constant weight was achieved. Absorption of synthetic skin oil by the PVC may result in a net weight gain, in which case the weight loss is reported as a negative number. The results are reported in Table 2 and the reported percent mass loss is an average of multiple tests.

TABLE 2

Percentage weight loss of material from sound transmission tubes extracted with a synthetic skin oil formulation.

| PVC tubing type | Coating type | Extraction time | Mass loss |
|---|---|---|---|
| Comparative Sample 1 | None (Comparative) | 7 days | 5.5% |
| Comparative Sample 2 | None (Comparative) | 7 days | 5.2% |
| Comparative Sample 3 | None (Comparative) | 7 days | 6.7% |
| Sample B | Parylene-N | 4 days | 0.1% |
| | | 7 days | −0.3% |
| Sample N | Parylene-C | 4 days | −0.4% |
| | | 7 days | −2.2% |

Sample Preparation

A dip-molded PVC tube was made by immersing a silicone-coated metal rod heated to over 400° F. (204° C.) into a plastisol formulation provided in Table 3.

The rod was slowly dipped into the plastisol formulation and slowly removed. It was subsequently heated in an oven at 330° F. (166° C.) for 9 minutes. The PVC tube was subsequently cooled and pulled off the rod. The tube had an inner diameter of approximately 5 mm and an outer diameter of 9-10 mm. The exterior of each tube was wiped clean with isopropanol. Three tube colors were made using STAN-TONE pigments available from PolyOne.

The tubes were cut into sections approximately 1.5 inch (3.8 cm) in length. The ends of the tubing sections were sealed by pressing the end onto a piece of aluminum foil on top of a hotplate set at 220° C. This melted the end and the pressure applied deformed and sealed the end. After cooling the foil was removed.

opening on top filled by a silicone gel pad with dimensions of 130 millimeters diameter×30 millimeters thick. The silicone gel pad was used to simulate human skin/flesh and was made from ECOLFEX 00-10 Super Soft Shore 00-10 Platinum Silicone Rubber Compound, available from Reynolds Advanced Materials of Countryside, IL, USA. A 3M LITTMANN CARDIOLOGY IV Stethoscope (available from 3M Company of St. Paul, MN) was used with each of the example stethoscope assembly tested. The stethoscope chestpiece assembled with each example tube was placed on the gel pad. A select weight was applied to the top of the chest piece. The applied weight represented light force (100 grams). The stethoscope ear tips were inserted into the ears of a Head simulator. Microphones in the ear couplers detected the stethoscope sound as in a manner equivalent to the human ear and a reference microphone positioned above the loudspeaker provided a normalization signal for the transfer function frequency response.

Sounds were generated, recorded and characterized by a Brüel & Kjaer (B&K) LAN-XI acoustic test system which operates with a PC using B&K PULSE software. An audio amplifier was used to drive the loudspeaker with sound produced by the LAN-XI system. The sounder cylinder with speaker inside was positioned on a 600 millimeter×900 millimeter Newport IsoStation Vibration Isolation Workstation. A transfer function frequency response curve was generated for each Example with a 100 gram weight used to apply a force to the chestpiece resting on the gel pad.

Figure 5:
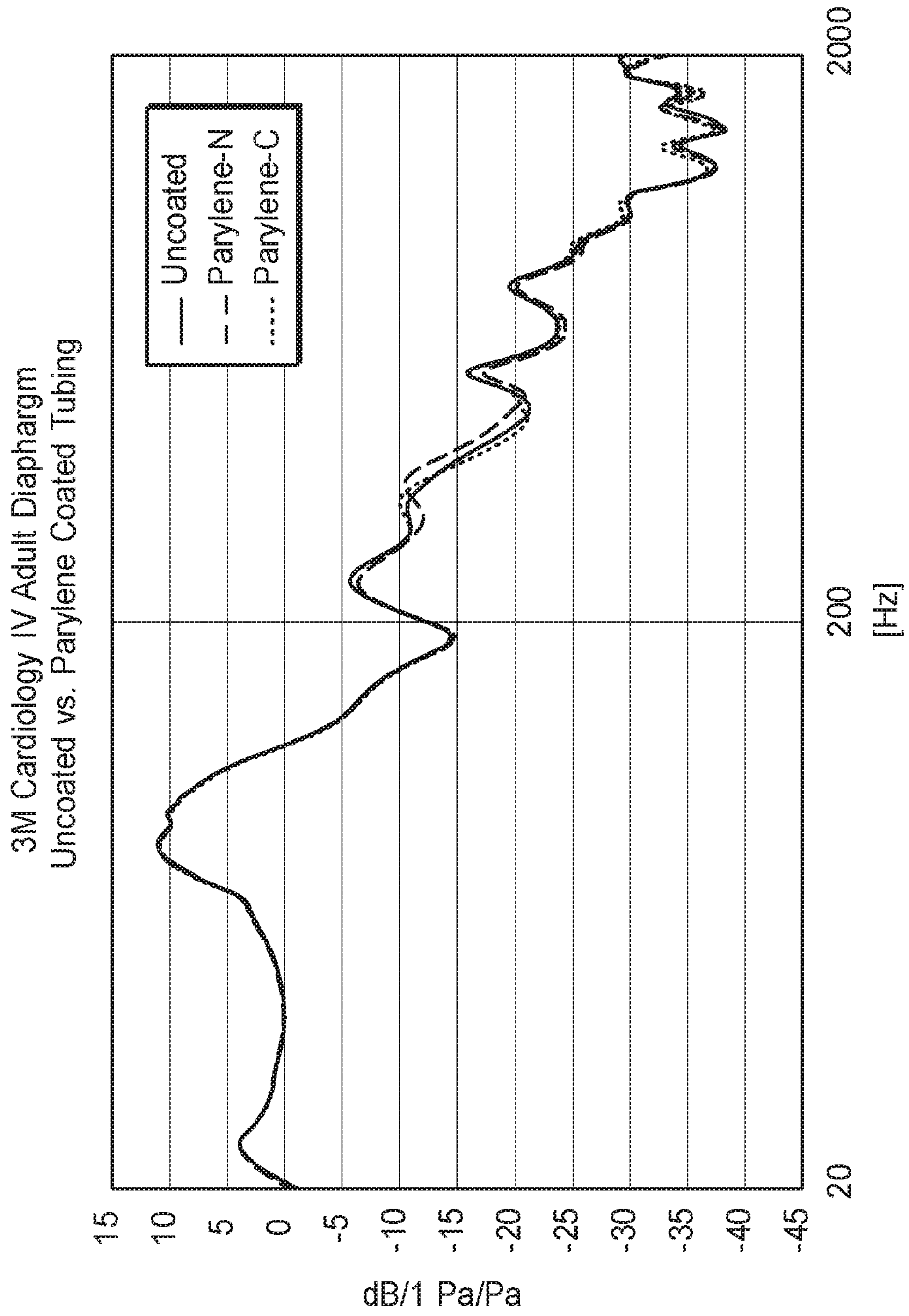
FIG. 5 is a graphical representation of acoustic performance data for comparative (uncoated) stethoscopes and stethoscopes of this disclosure (coated).

Results for the adult-sized diaphragm using light force are shown in FIG. 5. All samples were tested using the same Cardiology IV chestpiece and adult diaphragm. FIG. 5 shows a transfer function frequency response curves for the Cardiology IV stethoscope chestpiece assembled with

TABLE 3

Plastisol formulation.

| Material (Source, Location) | Trade name or abbreviation | Weight Percentage of Formulation |
|---|---|---|
| Plasticizer (Lanxess Corp., Pittsburgh, PA) | MESAMOLL | 41.44% |
| Poly(vinyl chloride) homopolymer resin (Formosa Plastics Corp. USA, Livingston, NJ) | FORMOLON-40 | 33.15% |
| Poly(vinyl chloride-co-vinyl acetate) (Arkema, Inc., King of Prussia, PA) | ISTAVIL 440 | 22.10% |
| Stabilizers | Proprietary | 2.32% |
| Pigments (PolyOne, Avon Lake, OH) | STAN-TONE | 0.96% |
| Viscosity modifier | Proprietary | 0.03% |

Acoustic Performance

Acoustics testing was performed on Cardiology IV stethoscopes assembled from uncoated sound transmission tubes (comparative examples) and from sound transmission tubes coated with Parylene-N and with Parylene-C. Frequency response was measured with light pressure using the Test Method as shown below.

Stethoscope Acoustic Testing Apparatus and Procedure

Figure 4:
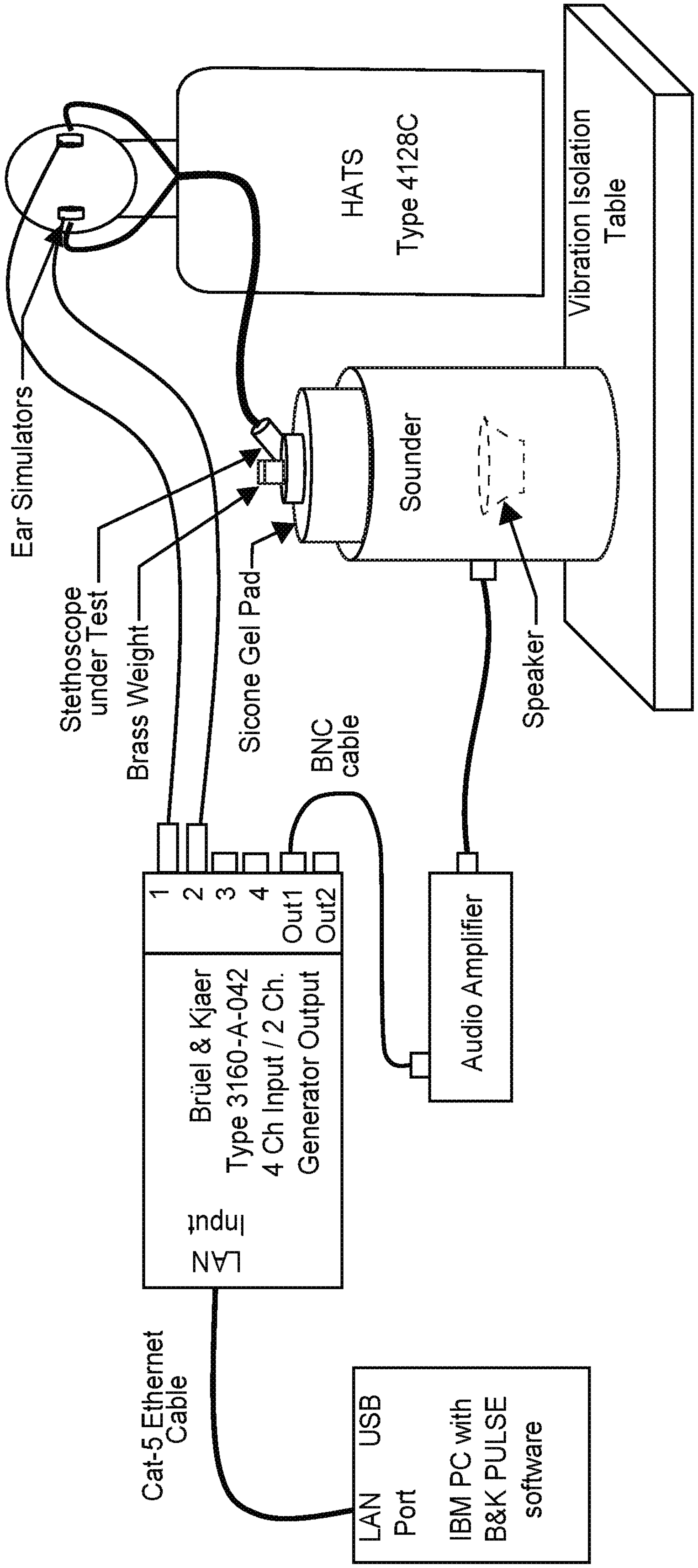
FIG. 4 is a diagram of a laboratory test set-up to generate an autospectrum frequency response of stethoscopes using one piece diaphragms.

Acoustic performance of a stethoscope can be described in terms of its frequency response to a broadband or pink noise source coupled to the chestpiece in a manner that simulates the human torso. The test apparatus used to characterize the acoustic performance is illustrated in FIG. 4. The equipment included: a Brüel & Kjær Head and Torso Simulator (HATS) type 4128C with 4159C Left Ear Simulator, 4158C Right Ear Simulator, and Calibrated Left and Right pinnae. The sound source was a loudspeaker enclosed in a cylindrical sounder chamber with an 87 millimeter uncoated tubes (comparative examples) and from tubes coated with Parylene-N and with Parylene-C. Virtually identical frequency response curves for all samples demonstrated that there is no change in the functional acoustic performance of stethoscope tubes coated with a Parylene coating.

Coefficient of Friction (COF) Testing of Flat Sheets

Flat sheet samples of uncoated PVC films prepared with the plastisol formulation shown in Table 3 and parylene-coated PVC films (prepared from the plastisol formulation shown in Table 3 and coated with parylene-C using the parylene coating method described above) were tested for coefficient of friction against simulated hair and skin substrates using the test method described below which is a variation of ASTM D1894.

CoF Test Method

The flat film samples were prepared by curing PVC plastisol at 350° F. (177° C.) for 10 minutes between 2

PYREX sheets with a 0.25 inch (0.64 cm) rubber spacer between the PYREX sheets. The parylene coated samples were prepared as described above. Upon cooling, a sample of 6.25×12 inches (16×30 cm) was cut from the cured sheet.

The hair samples were Hairstrips 3 inches (7.6 cm) wide, 6 inches (15 cm) long, and 1 inch (2.5 cm) thick from Spectrum Brands; Madison, WI. The Hairstrips were acclimated in the testing room for at least 4 days.

The simulated skin samples were 2 inch (5 cm) wide strips of VITRO-SKIN from IMS, Bunnell, FL that were hydrolyzed by placing in a sealed container with a container of water for at least 16 hours. A VITRO-SKIN strip was wrapped around a 200 gram sled and adhered to the sled with double-sided tape.

The testing was carried out on an IMASS Peel Tester (SP-2100) for 5.30 inches (13 cm) at a rate of 6 inches per minute (15 cm/min). The PVC sample tested was secured to the peel tester platform.

For the hair testing, an arm with a clamp was attached to the peel tester sensor, and the Hairstrip was attached to the clamp. The PVC sample was then dragged across the hair sample.

For the VITRO-SKIN testing, the VITRO-SKIN-wrapped sled was attached to the peel tester sensor. The PVC sample was then dragged across the VITRO-SKIN sample.

Three trials were carried out and the average value for the peak force is presented as the coefficient of friction in Table 7 below.

TABLE 4

| Sample | | Average CoF |
|---|---|---|
| Comparative | Skin | 0.985 |
| (non-coated) | Hair | 1.707 |
| Example | Skin | 0.449 |
| (Coated) | Hair | 0.317 |

Silicone Stethoscope Tube with Parylene Coating

A silicone sound transmission tube was coated with Parylene-C on a rotating carousel according to the process described above. The resulting Parylene-C coated silicone sound transmission tube had a matte appearance and was less tacky/sticky to the touch than the uncoated tube. The acoustic performance of the parylene-coated and uncoated ear tubes was indistinguishable.

What is claimed is:

1. A medical article comprising:

a tube with an interior surface and an exterior surface, comprising a polymer composition containing one or more extractable components; and a vapor-deposited coating of a barrier polymer which comprises a copolymer of parylene and at least one alkyl (meth)acrylate covering at least a portion of at least the exterior surface of the tube, such that the vapor-deposited polymer coating barrier reduces the extraction of extractable component(s) from the tube.

2. The medical article of claim 1, wherein the polymer composition containing one or more extractable components comprises:

plasticized polyvinyl chloride (PVC);

plasticized PVC copolymers;

plasticized polyurethane; or polysiloxane containing unreacted cyclic siloxane, catalyst residue, plasticizer, tackifier, or a combination thereof.

3. The medical article of claim 2, wherein the polymer composition containing one or more extractable components comprises plasticized PVC free of phthalate plasticizer.

4. The medical article of claim 2, wherein the polymer composition containing one or more extractable components comprises plasticized PVC wherein the plasticized PVC comprises at least 25% plasticizer by weight.

5. The medical article of claim 2, wherein the polymer composition containing one or more extractable components comprises plasticized PVC wherein the plasticized PVC comprises at least 40% plasticizer by weight.

6. The medical article of claim 1, wherein parylene comprises parylene N or parylene C.

7. The medical article of claim 1, wherein the vapor-deposited barrier polymer coating has a thickness of from 1-10 micrometers.

8. The medical article of claim 1, wherein the vapor-deposited barrier polymer coating has a thickness of from 2-5 micrometers.

9. The medical article of claim 1, wherein the vapor-deposited barrier polymer coating further comprises at least one anti-microbial agent.

10. The medical article of claim 1, wherein the polymer composition containing one or more extractable components has a thickness of from 0.1-7 millimeters.

11. The medical article of claim 1, wherein the tube comprises tubing for a stethoscope.

12. The medical article of claim 1, wherein the vapor-deposited coating changes the color, the texture, the coefficient of friction, the optical appearance of the tubing, or a combination thereof.

13. The medical article of claim 1, wherein the reduction of extraction of extractable component(s) from the tube comprises a reduction in solvent extraction by polar or nonpolar solvent.

14. The medical article of claim 1, wherein the at least one (meth) acrylate comprises at least one C3-C18 alkyl (meth) acrylate.

15. A method of preparing a medical article comprising:

providing a tube with an interior surface and an exterior surface, comprising a polymer composition containing one or more extractable components; and vapor coating a barrier polymer which comprises a copolymer of parylene and at least one alkyl (meth)acrylate onto at least a portion of at least the exterior surface of the tube, such that the coating reduces the extraction of extractable component(s) from the tube.

16. The method of claim 15, wherein vapor coating a barrier polymer onto at least a portion of at least the exterior surface of the tube comprises:

placing the tube in a deposition chamber;

applying a vacuum to the deposition chamber;

heating a precursor material to volatize at least a portion of it; and introducing the volatilized precursor material into the deposition chamber, wherein the precursor material comprises parylene or a mixture of parylene and at least one (meth)acrylate.

17. The method of claim 16, wherein placing the tube in a deposition chamber comprises placing the tube in a rotating basket or hanging the tube from a rack.

18. The method of claim 15, wherein the coating has a thickness of from 1-10 micrometers.

19. The method of claim 15, wherein the tube comprises tubing for a stethoscope.

* * * * *